United States Patent
Oshikawa et al.

(10) Patent No.: US 11,988,680 B2
(45) Date of Patent: May 21, 2024

(54) ANALYTICAL OPERATION ASSISTING DEVICE AND NON-TRANSITORY COMPUTER READABLE MEDIUM RECORDING ANALYTICAL OPERATION ASSISTING PROGRAM

(71) Applicant: SHIMADZU CORPORATION, Kyoto (JP)

(72) Inventors: Tomonori Oshikawa, Kyoto (JP); Yuko Kobayashi, Kyoto (JP); Yoshiki Tainaka, Kyoto (JP); Tatsuki Okubo, Kyoto (JP); Kohei Suzuki, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 512 days.

(21) Appl. No.: 17/376,776

(22) Filed: Jul. 15, 2021

(65) Prior Publication Data

US 2022/0065884 A1    Mar. 3, 2022

(30) Foreign Application Priority Data

Sep. 1, 2020   (JP) .................................. 2020-146824

(51) Int. Cl.
*G01N 35/00* (2006.01)
*G01N 33/49* (2006.01)
(Continued)

(52) U.S. Cl.
CPC ....... *G01N 35/00871* (2013.01); *G01N 33/49* (2013.01); *H01J 49/164* (2013.01); *H01J 49/40* (2013.01); *G01N 2035/00891* (2013.01)

(58) Field of Classification Search
None
See application file for complete search history.

(56) References Cited

U.S. PATENT DOCUMENTS

| 10,338,897 | B2 * | 7/2019 | Javadi | ........................ G06F 8/34 |
| 2017/0184573 | A1 | 6/2017 | Kaneko et al. | |
| 2018/0253194 | A1 * | 9/2018 | Javadi | ........................ G06F 8/38 |

FOREIGN PATENT DOCUMENTS

WO    2015/178398 A1    11/2015

OTHER PUBLICATIONS

Notice of Allowance dated Oct. 3, 2023 issued for the corresponding Japanese Patent Application No. 2022-546886.
(Continued)

*Primary Examiner* — Andrew Smyth
(74) *Attorney, Agent, or Firm* — Sughrue Mion, PLLC

(57) ABSTRACT

In a device (4) for assisting in analytical operations for correctly arranging samples in a plurality of sample-placement portions and implementing multiple protocols in the correct order, a storage section (41) holds sample information and analysis parameters for each protocol as well as the order of implementation. A protocol-selection-input receiver (42) receives an input of the selection of a protocol. A sample-position displayer (43) displays, on a display unit (6), sample information in the selected protocol along with the positions of the sample-placement portions. A protocol-implementation-information collector (45) collects information concerning the state of implementation of the protocols. A determiner (46) determines whether a protocol which must be implemented earlier was already implemented, based on the state of implementation and order of implementation of the protocols. A batch-file creator (47) creates a batch file when it is confirmed that the protocol which must be implemented earlier was already implemented.

6 Claims, 6 Drawing Sheets

(51) Int. Cl.
*H01J 49/16* (2006.01)
*H01J 49/40* (2006.01)

(56) References Cited

OTHER PUBLICATIONS

Written Opinion of PCT/JP2021/016671 dated Jun. 22, 2021 [PCT/ISA/237].
International Search Report of PCT/JP2021/016671 dated Jun. 22, 2021 [PCT/ISA/210].
Akinori Nakamura et al., "High performance plasma amyloid-ß biomarkers for Alzheimer's disease", Nature, 2018, pp. 249-254.
Notice of Allowance dated Aug. 1, 2023 in Japanese Application No. 2020-146824.

* cited by examiner

ANALYTICAL OPERATION ASSISTING DEVICE AND NON-TRANSITORY COMPUTER READABLE MEDIUM RECORDING ANALYTICAL OPERATION ASSISTING PROGRAM

TECHNICAL FIELD

The present invention relates to a technique for assisting in analytical operations.

BACKGROUND ART

Alzheimer's disease is known as a disease that causes dementia. A patient with Alzheimer' disease suffers from gradual deterioration in memory and recognition as well as other related symptoms. Therefore, it is useful to detect Alzheimer' disease in its early stage and begin appropriate treatments before the onset of dementia.

Patients with Alzheimer's disease are known to have a substance called "amyloid beta" accumulated in their brains (for example, see Non Patent literature 1). Positron-emission tomography (PET) scanners have conventionally been used for checking the state of the accumulation of amyloid beta in the brain. However, the PET check requires a long period of time and is considerably expensive. To address this problem, Patent Literature 1 proposes a method in which the intensities of ions that respectively originate from two specific kinds of peptides contained in a blood sample taken from a subject are measured by mass spectrometry, and the intensity ratio of those ions are evaluated to check the state of the accumulation of amyloid beta. This method allows for the diagnosis of Alzheimer's disease to be performed more quickly and less expensively than the method which uses PET. It also enables successive and efficient diagnosis of Alzheimer's disease for a plurality of subjects.

The method described in Patent Literature 1 uses a MALDI-TOF mass spectrometer. In a MALDI-TOF mass spectrometer, a sample to which a matrix has been added is placed in a well of a sample plate and irradiated with laser light to ionize the sample (MALDI). The resulting ions are introduced into a time-of-flight (TOF) mass separation unit. The various kinds of ions introduced into the mass separation unit fly in the TOF space for different periods of time depending on their respective mass-to-charge ratios until they are ultimately detected.

As noted earlier, the method described in Patent Literature 1 checks the state of the accumulation of amyloid beta by measuring the intensities of ions which respectively originate from two specific kinds of peptides contained in a blood sample taken from a subject. In order to correctly perform this check, it is necessary to correctly determine the position and intensity of the mass peak of each ion. That is to say, the mass spectrometric analysis of the sample always needs to be performed with a constant level of mass accuracy and sensitivity. When it is required to guarantee that the level of mass accuracy and sensitivity is constant, the mass spectrometric analysis should follow a standard operation procedure (SOP) specified beforehand for the analysis.

An example of the standard operation procedure for a mass spectrometric analysis of samples using a MALDI-TOF mass spectrometer is hereinafter described. A sample plate to be used for MALDI is divided into a large number of individual areas having a square shape. Each individual area has a central well in which a calibrant is to be placed, surrounded by four wells in each of which a sample is to be placed. A calibrant is a substance which produces an ion having a known mass-to-charge ratio to be used for the mass calibration.

Initially, the first protocol for determining an optimum intensity of the laser light for ionizing a sample is carried out. The first protocol uses the same number of individual areas on the sample plate as the number of previously set candidate values of the intensity of the laser light. A standard sample containing a specified amount of target substance is placed in the four surrounding wells in each individual area, while a calibrant is placed in the central well. In the first protocol, the same standard sample and calibrant are placed in all individual areas. The sample plate on which the standard sample and calibrant have been placed is subsequently set in a mass spectrometer. Then, the calibrant placed in the first individual area is irradiated with the laser light whose intensity equals one of the candidate values. The result of the detection of the resulting ion is compared with the actual mass-to-charge ratio of the ion to mass-calibrate the mass spectrometer. After the measurement of the calibrant each of the samples placed in the four other wells in the same individual area is also similarly irradiated with the laser light whose intensity equals the aforementioned candidate value, and the resulting ions are detected. Subsequently, an average of the detection intensities of each ion obtained by the four mass spectrometric analyses is calculated, and the ion-detection sensitivity for the laser light having the intensity concerned is determined from the detection intensity of an ion having a previously specified mass-to-charge ratio. Such a mass spectrometric analysis is similarly performed on each of the standard samples placed in all individual areas using a different candidate value of the intensity of the irradiation laser light for each individual area, to determine the ion-detection sensitivity for each candidate value of the intensity of the laser light. Based on the result, the intensity of the laser light to be used for irradiating an actual sample is determined. In normal cases, the candidate value of the intensity of the laser light which yields the highest level of detection sensitivity is selected.

After the intensity of the laser light for irradiating samples has been determined, the second protocol for determining a correction value related to the relationship between the content of the target substance and the detection intensity of an ion is carried out. The second protocol uses a plurality of standard samples which respectively contain different specified amounts of target substance, and also uses the same number of individual areas as the standard samples. The same standard sample is placed in the four wells of each individual area, while the calibrant is placed in the central well. The same calibrant is used for all the individual areas. The sample plate on which the standard samples and calibrant have been placed is subsequently set in the mass spectrometer. Then, the calibrant placed in the first individual area is irradiated with the laser light having the intensity determined in the previous protocol, and the mass calibration of the mass spectrometer is performed in the same manner as in the first protocol. After the measurement of the calibrant, the laser irradiation is similarly performed for each of the standard samples placed in the four other wells in the same individual area, using the laser light having the intensity value determined in the first protocol. An average of the detection intensities of each ion obtained by the four mass spectrometric analyses is calculated, and the relationship between the content of the target substance in the standard sample and the detection intensity of the ion is determined from the detection intensity of an ion having a previously specified mass-to-charge ratio. Such a series of mass spectrometric analyses are performed on each of the individual areas concerned, and a correction value for the detection intensity is determined so that the detection intensities of the ions originating from each specified amount of target substance will be previously determined intensities.

After the two previously described protocols have been carried out, the third protocol for performing mass spectrometric analyses of measurement-target samples is implemented. In the third protocol, the standard sample is placed in the first individual area. The measurement-target samples are sequentially placed in the second and subsequent individual areas. After a predetermined number of measurement-target samples have been placed, the standard sample is once more placed in the next individual area. That is to say, the standard sample and measurement-target samples are arranged so that a measurement for the standard sample is performed for every completion of the measurement of the predetermined number of measurement-target samples. The standard sample is used for confirming that the mass spectrometric analysis is being correctly performed at each point in time. As in the two foregoing protocols, a calibrant for mass calibration is placed in each individual area in the third protocol. The mass spectrometric analysis is sequentially performed from the first individual area, in which the measurement-target samples placed in the four wells in the individual area are individually irradiated with laser light having the intensity determined in the first protocol. An average of the detection intensities of each ion obtained by the four mass spectrometric analyses is calculated. The detection intensity of an ion having a previously specified mass-to-charge ratio is corrected with the correction value determined in the second protocol, to determine the intensities of the ions originating from the target substance contained in the measurement-target sample.

CITATION LIST

Patent Literature

Patent Literature 1: WO2015/178398 A

Non Patent Literature

Non Patent Literature 1: Akinori Nakamura, Naoki Kaneko, Victor L. Villemagne, Takashi Kato, James Doecke, Vincent Dore, Chris Fowler, Qiao-Xin Li, Ralph Martins, Christopher Rowe, Taisuke Tomita, Katsumi Matsuzaki, Kenji Ishii, Kazunari Ishii, Yutaka Arahata, Shinichi Iwamoto, Kenuo Ito, Koichi Tanaka, Colin L. Masters, and Katsuhiko Yanagisawa, "High performance plasma amyloid-β biomarkers for Alzheimer's disease", Nature, 2018, 554, pp. 249-254

SUMMARY OF INVENTION

Technical Problem

In the method described in Patent Literature 1, the first through third protocols need to be carried out in the correct order. Furthermore, the samples need to be correctly arranged in the wells within each individual area when each protocol is carried out. When this method is carried out by an individual who is not accustomed to this type of analysis, the protocols may possibly be carried out in an incorrect order, or some samples may be placed in the wrong well s.

Although the previous descriptions have been concerned with the case of performing a mass spectrometric analysis of samples using a MALDI-TOF mass spectrometer, the previously described problems can also occur in an analysis of samples using a different type of analyzing device.

The problem to be solved by the present invention is to provide a technique for assisting a user in analytical operations so that the user can correctly place samples in a plurality of sample-placement portions provided in a sample-containing member and implement a plurality of protocols in the correct order.

Solution to Problem

The present invention developed for solving the previously described problem is an analytical operation assisting device configured to be capable of communicating with an analyzing device in which a sample-containing member is to be set, and to assist a user in analytical operations which include arranging samples in a plurality of sample-placement portions provided in the sample-containing member and sequentially implementing a plurality of protocols, the analytical operation assisting device including:

a storage section in which analysis conditions and information concerning the order of implementation of the plurality of protocols are stored, the analysis conditions including information concerning samples to be arranged in each of the plurality of protocols and an analysis parameter;

a display unit;

a protocol-selection-input receiver configured to receive an input of the selection of one of the plurality of protocols;

a sample-position displayer configured to read, from the storage section, the information concerning the samples to be arranged in the protocol inputted through the protocol-selection-input receiver, and to display, on the display unit, the read information along with the positions of the plurality of sample-placement portions provided in the sample-containing member;

a protocol-implementation-information collector configured to collect, from the analyzing device, information concerning the state of implementation of the plurality of protocols;

a determiner configured to determine whether or not a protocol which must be implemented earlier than the protocol inputted through the protocol-selection-input receiver was already implemented, based on the state of implementation of the plurality of protocols collected by the protocol-implementation-information collector and the order of implementation of the plurality of protocols stored in the storage section; and a batch-file creator configured to read, from the storage section, the analysis conditions corresponding to the protocol inputted through the protocol-selection-input receiver and to create a batch file for implementing the selected protocol, when it is determined by the determiner that the protocol which must be implemented earlier was already implemented.

Another aspect of the present invention developed for solving the previously described problem is a non-transitory computer readable medium recording a program for enabling a computer to communicate an analyzing device in which a sample-containing member is to be set, and for assisting a user in analytical operations which include arranging samples in a plurality of sample-placement portions provided in the sample-containing member and sequentially implementing a plurality of protocols, where the computer includes:

a storage section in which analysis conditions and information concerning the order of implementation of the plurality of protocols are stored, the analysis conditions including information concerning samples to be arranged in each of the plurality of protocols and an analysis parameter; and a display unit;

and the program is configured to make the computer function as:

a protocol-selection-input receiver configured to receive an input of the selection of one of the plurality of protocols;

a sample-position displayer configured to read, from the storage section, the information concerning the samples to be arranged in the protocol inputted through the protocol-selection-input receiver, and to display, on the display unit, the read information along with the positions of the plurality of sample-placement portions provided in the sample-containing member;

a protocol-implementation-information collector configured to collect, from the analyzing device, information concerning the state of implementation of the plurality of protocols;

a determiner configured to determine whether or not a protocol which must be implemented earlier than the protocol inputted through the protocol-selection-input receiver was already implemented, based on the state of implementation of the plurality of protocols collected by the protocol-implementation-information collector and the order of implementation of the plurality of protocols stored in the storage section; and a batch-file creator configured to read, from the storage section, the analysis conditions corresponding to the protocol inputted through the protocol-selection-input receiver and to create a hatch file for implementing the selected protocol, when it is determined by the determiner that the protocol which must be implemented earlier was already implemented.

Advantageous Effects of Invention

According to the present invention, when a user selects one of the plurality of protocols previously stored in the storage section, the sample-position displayer reads, from the storage section, the information concerning the samples to be arranged in the selected protocol, and displays the read information along with the positions of the plurality of sample-placement portions provided in the sample-containing member. For example, in the case of where the sample plate has a plurality of sample-placement portions arranged in a lattice form, the sample information is displayed on the same number of sample-placement portions as the samples to be arranged in the protocol concerned, starting from the sample-placement portion located at the upper-right corner of the sample plate displayed in a predetermined orientation on the screen. Therefore, when implementing each protocol, the user can conveniently understand which sample should be placed at which position, and correctly arrange the samples.

Furthermore, according to the present invention, when a protocol is selected by the user, whether or not a protocol which must be implemented earlier than the selected protocol was already implemented is determined by the determiner. When it is confirmed that the protocol which must be implemented earlier was already implemented, a batch file for implementing the protocol selected by the user is created. In other words, if the user selects a protocol without implementing another protocol which must be implemented earlier, the batch file for implementing the selected protocol will not be created. Therefore, the user can be appropriately instructed to implement the plurality of protocols in the correct order.

DESCRIPTION OF EMBODIMENTS

An embodiment of the analytical operation assisting device and program according to the present invention is hereinafter described with reference to the drawings. The analytical operation assisting device and program according to the present embodiment are used for assisting a user in a series of analytical operations in which the intensities of ions that respectively originate from two specific kinds of peptides contained in a blood sample taken from a subject are measured by mass spectrometry, and the intensity ratio of those ions are evaluated to check the state of the accumulation of amyloid beta.

Figure 1:
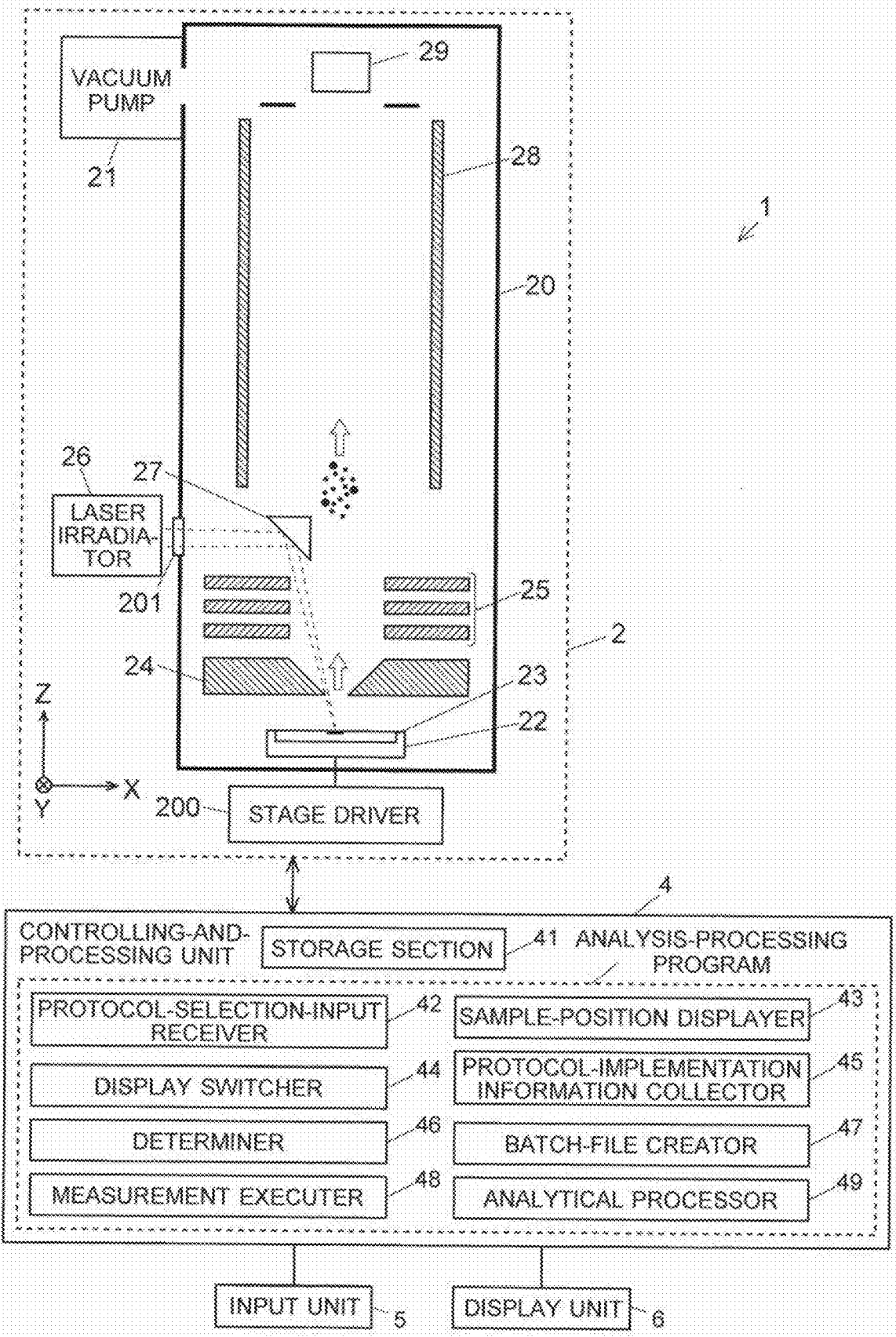
FIG. 1 is a configuration diagram showing the main components of an analyzing system including one embodiment of the analytical operation assisting device and program according to the present invention.

FIG. 1 is a configuration diagram showing the main components of an analyzing system 1 including the analytical operation assisting device and program according to the present embodiment. The analyzing system 1 roughly consists of an analyzing unit 2 and a controlling-and-processing unit 4. The analytical operation assisting device and program are included in a section of the controlling-and-processing unit 4.

Thea analyzing unit 2 is a MALDI-TOF mass analyzer in which a MALDI ion source is combined with time-of-flight mass separator (TOF).

The analyzing unit 2 includes a chamber 20 to be evacuated by a vacuum pump 21. The chamber 20 contains a sample stage 22 configured to hold a sample plate 23, an extraction electrode 24, an acceleration electrode 25, a flight tube 28 forming a flight space inside, and a detector 29. A window 210 for allowing light to pass through within the wavelength range of the laser light (which will be described later) is provided in the wall of the chamber 20. A laser irradiator 26 including a laser source is located at the window 201 on the outside of the chamber 20, while a mirror 27 is located within the chamber 20 and opposite to the laser irradiator 26 across the window 201. The sample stage 22 can be driven in the horizontal direction (X-axis and Y-axis directions) as well as in the vertical direction (Z-axis direction) by a stage driver 200 including a motor.

In a measurement of a sample, the sample stage 22 is driven by the stage driver 200 so that the well in which the target sample is present on the sample plate 23 held on the sample stage 22 is adjusted at the irradiation point of the laser light. A beam of laser light with a previously specified intensity is subsequently generated from the laser irradiator 26 for a predetermined period of time. After passing through the window 201, the beam of laser light is deflected downward by the mirror 27. The deflected beam hits the sample in the well on the sample plate 23.

Upon being irradiated with the laser light, the components in the sample are turned into vapor and ionized. The ions derived from the sample components are vertically extracted (in the Z-axis direction) from an area near the surface of the sample plate 23 due to the effect of the electric field created by the direct voltage applied from a power unit (not shown) to the extraction electrode 24. Those ions reach the acceleration electrode 25, where each ion is given a specific amount of kinetic energy due to the effect of the acceleration electric field created by the direct voltages applied from a power unit (not shown) to the acceleration electrode 25. The ions are thereby accelerated vertically (in the Z-axis direction), to be introduced into the flight space with no electric/magnetic field inside the flight tube 28. While flying in this flight space, the ions are temporally separated from each other according to their mass-to-charge ratios m/z. The separated ions sequentially arrive at the detector 29 and are detected by the same detector 29. The detector 29 produces detection signals corresponding to the amounts of ions it has received. The signals thus produced are sequentially stored in a storage section 41 (which will be described later).

The controlling-and-processing unit 4 includes, in addition to the storage section 41, a protocol-selection-input receiver 42, sample-position displayer 43, display switcher 44, protocol-implementation-information collector 45, determiner 46, batch-file creator 47, measurement executer 48 and analytical processor 49 as its functional blocks. The controlling-and-processing unit 4 is actually a common personal computer, on which the aforementioned functional blocks are embodied by running a pre-installed analysis program on a processor of the computer. Additionally, an input unit 5 (including a keyboard, mouse and other devices) for allowing a user to perform input operations and a display unit 6 (including a liquid crystal display and other related devices) are connected to the controlling-and-processing unit 4.

The storage section 41 holds information concerning four kinds of analysis protocols. The four kinds of analysis protocols are prepared for performing the laser-power selection, intensity-ratio calibration, standard plasma analysis, and specimen analysis, respectively. The information of the order of implementation of the analysis protocols is also stored in the storage section 41. In the present embodiment, it is prescribed that the analysis protocols for laser-power selection, intensity-ratio calibration, standard plasma analysis, and specimen analysis should be implemented in the mentioned order. It is also prescribed that the standard plasma analysis may be omitted (i.e., the specimen analysis can be performed even when the standard plasma analysis is not performed).

The storage section 41 holds information concerning the samples (such as the kind and name of each sample) and information concerning analysis parameters to be used in each of the four analysis protocols. The information stored for the laser-power selection includes the use of a standard sample containing specified amounts of peptides which are the measurement targets, as well as analysis parameters including five setting values (−10, −5, 0, +5 and +10) related to the laser power. The five setting values (−10, −5, 0, +5 and +10) related to the laser power are the values to be added to or subtracted from a reference value of the laser power, which is entered by the user when determining the intensity of the laser light for irradiating samples in the analysis protocol for laser-power selection (which will be described later).

The information stored for the intensity-ratio calibration includes the use of five kinds of standard samples (IC-1, IC-2, IC-3, IC-4 and IC-5) containing different amounts of peptides which are the measurement targets, as well as analysis parameters including a laser-power value based on the result of the analytical processing in the foregoing analysis protocol (laser-power selection).

The information stored for the standard-plasma analysis includes the use of a standard plasma as well as analysis parameters including a laser-power value based on the result of the analytical processing in the foregoing analysis protocol (laser-power selection). A "standard plasma" is prepared through a pretreatment of human plasma. The term "standard" means that the plasma contains known amounts of peptides which are the measurement targets.

The information stored for the specimen analysis includes the use of the standard plasma and plasma specimens extracted from blood samples taken from untested subjects, as well as analysis parameters including a laser-power value based on the result of the analytical processing in the foregoing analysis protocol (laser-power selection). For the present embodiment, it is assumed that measurement-target specimens 1-12 sampled from 12 subjects are used. The number of subjects can be changed as needed within the capacity of the sample plate 23.

Next, a procedure of an analysis using the analyzing system 1 according to the present embodiment is described. When the user issues a command to initiate an analysis, a screen as shown in FIG. 2 is displayed on the display unit 6, FIG. 2 is a display example in which the analysis protocol for specimen analysis is selected after the analysis protocols for laser-power selection and intensity-ratio calibration have been implemented.

Figure 2:
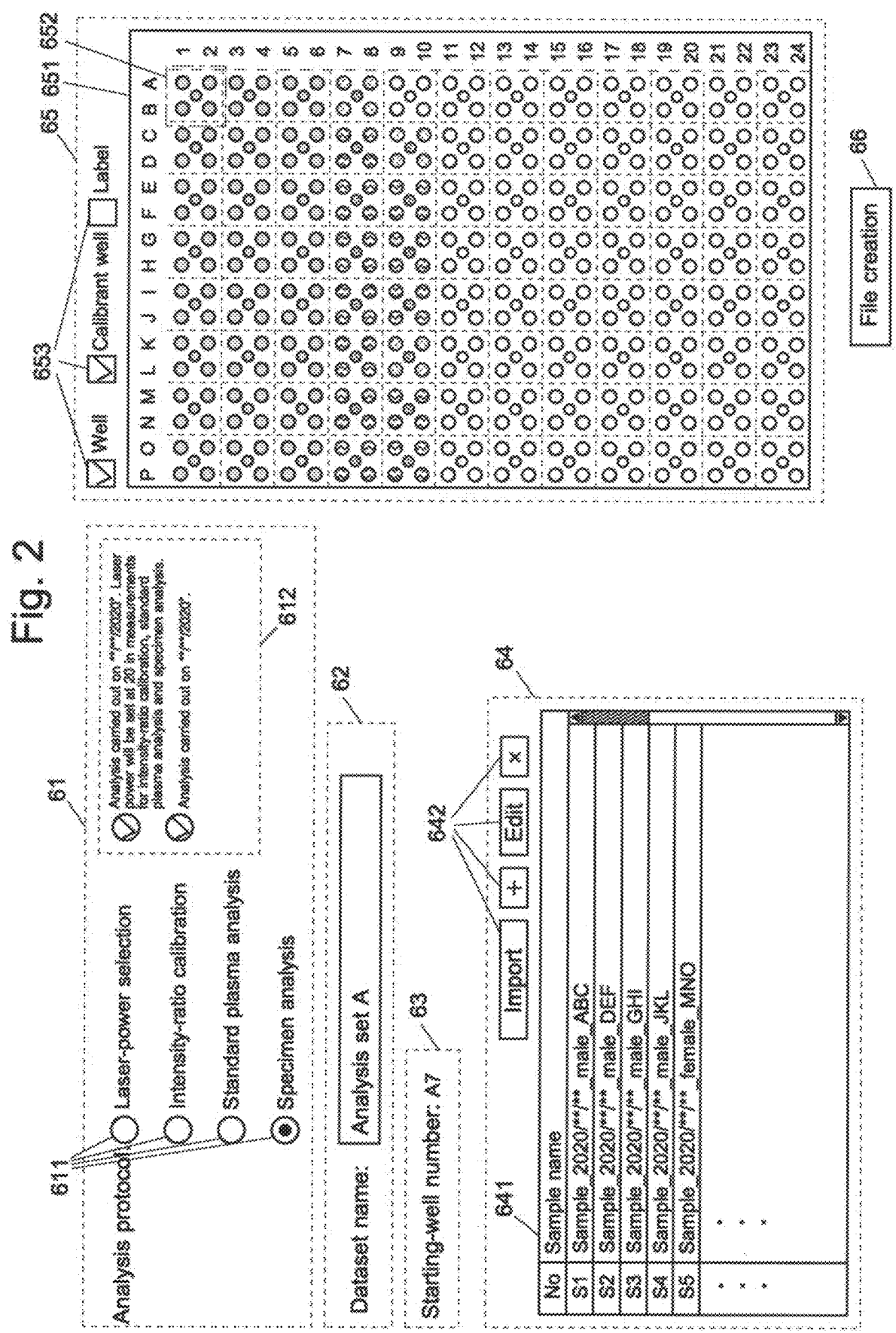
FIG. 2 is one example of the display screen in the analyzing system according to the present embodiment.

The screen shown in FIG. 2 includes an analysis-protocol selection section 61, dataset-name input section 62, starting-well-number display section 63, sample-information display section 64, and sample-plate display section 65.

The analysis-protocol selection section 61 shows the names of the four analysis protocols along with the corresponding selectors 611, as well as an analysis-protocol-implementation-information display area 612. When the user selects one of the four selectors 611, an input of the corresponding analysis protocol is received by the protocol-selection-input receiver 42. Meanwhile, information concerning the already implemented analysis protocols is displayed in the analysis-protocol-implementation-information display area 612.

The dataset-name input section 62 has an area for inputting the dataset name of the data acquired by implementing a series of analysis protocols. The starting-well-number display section 63 shows the position number of the well in which the first sample should be set in the next analysis protocol to be implemented. The sample-information display section 64 has a sample-name display area 641 and data-editing buttons 642. The sample-name display area 641 shows the relationship between the labels to be displayed in the sample-plate display section 65 (which will be described later) and the sample names of the samples selected in the analysis-protocol selection section 61. The data-editing buttons 642 include: an "Import" button for reading a file in which sample names are written and displaying those names in the sample-name display area 641; a "+" button for adding a display field to the sample-name display area 641; a "×" button for deleting a display field from the sample-name display area 641; and an "Edit" button for editing a sample name displayed in the sample-name display area 641.

The sample-plate display section 65 includes a sample-plate overview area 651 and a display item selector 653. In the sample plate used in the present embodiment, as shown in the sample-plate overview area 651, individual areas 652 in which samples are to be placed are arranged in a lattice form. The same type of sample should be placed in the wells located at the four corners of each individual well 652, while a calibrant is to be placed in the central well. A file creation button 66 for creating a batch file which implements each analysis protocol is displayed below the sample-plate display section 65.

Initially, the user selects the selector 611 of the first analysis protocol to be implemented (laser-power selection) among the analysis protocols displayed in the analysis-protocol selection section 61, whereupon an input of the protocol for laser-power selection is received by the protocol-selection-input receiver 42. In response to the selection of the analysis protocol, the determiner 46 reads the information of the implementation order of the analysis protocols stored in the storage section 41. Since the protocol for laser-power selection is the first analysis protocol to be implemented, the determiner 46 discontinues its operation without making any determination. The user also inputs the name of the dataset. A screen for inputting the reference value of the laser power, which will be used when the protocol for laser-power selection is implemented, is displayed on the display unit 6, prompting the user to input the value. For example, the reference value can be specified within a range of 15-170. For the following description, it is assumed that "15" has been entered as the reference value.

Subsequently, the sample-position displayer 43 reads, from the storage section 41, the sample information and analysis parameters corresponding to the analysis protocol (laser-power selection) received by the protocol-selection-input receiver 42. As noted earlier, the information stored for the protocol for laser-power selection includes the use of a standard sample containing specified amounts of peptides which are the measurement targets, as well as analysis parameters including five setting values (−10, −5, 0, +5 and +10) related to the laser power. After reading those pieces of information, the sample-position displayer 43 calculates five values by increasing or decreasing the user-inputted reference value of the laser power by the five setting values. The obtained values in the present example, 5, 10, 15, 20 and 25) are the values of the laser power to be actually used for irradiating samples. Those pieces of information are displayed at the positions of the wells in which samples are to be placed in the sample-plate overview area 651.

Figure 3:
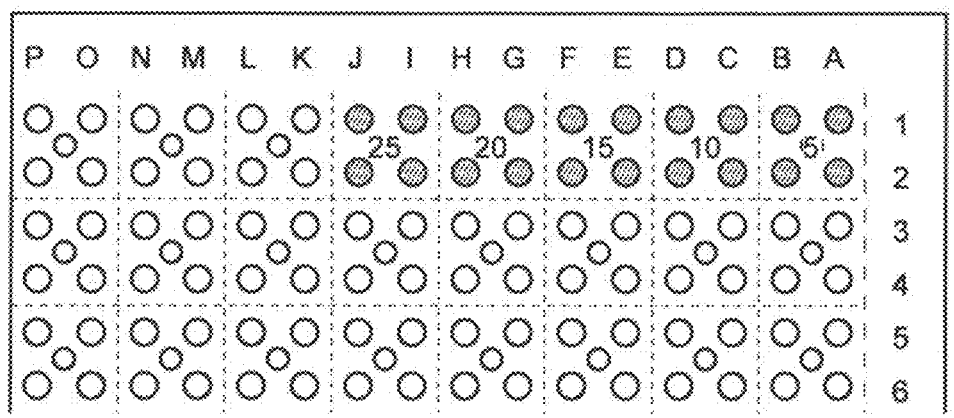
FIG. 3 is a display example of a sample-plate overview area which is displayed when an analysis protocol for laser-power selection is implemented in the present embodiment.

A display example of the sample-plate overview area 651 by the sample-position displayer 43 is shown in FIG. 3. In the present embodiment, the sample-position displayer 43 extracts five horizontally arranged individual areas starting from the individual area 652 located at the upper-right corner of the group of unused individual areas 652 (at this point in time, all wells are unused). Then, the sample-position displayer 43 shows, in the starting-well-number display section 63, the position number of the upper-right well in the starting individual area 652. This well, which is "A1" in the present case, is the well at which the sample measurement will be performed first among the four wells in which samples are to be placed within the individual area 652 concerned.

Next, the sample-position displayer 43 gives specific colors to the five wells in each of the five individual areas 652 in such a manner that the wells at the four corners are shown in yellow which indicates that the standard sample for laser-power selection should be placed in those wells, while the central well is shown in purple which indicates that the calibrant should be placed in this well. Since the attached drawings are prepared in black and white, the different colors are represented by different hatching patterns in FIG. 3 (which also applies to FIG. 4 and sequent figures). Additionally, a label is put on each individual area 652 to show the value of the laser power (5, 10, 15, 20 or 25, which have been calculated by increasing or decreasing the user-inputted reference value of the laser power by the five setting values) to be used for irradiating the standard sample and calibrant placed in the wells of each individual area. The display example in FIG. 3 shows a situation in which all items in the display-item selector 653 are checked. The type of label to be displayed on the individual areas 652 changes depending on the analysis protocol. In the case of arranging different samples in different individual areas 652, a label concerning each sample is displayed. In the case of arranging the same sample in all individual areas 652 and performing a measurement using a different value of an analysis parameter for each area, a label showing the value of that parameter is displayed. The analysis protocol for laser-power selection corresponds to the latter case.

Figure 4:
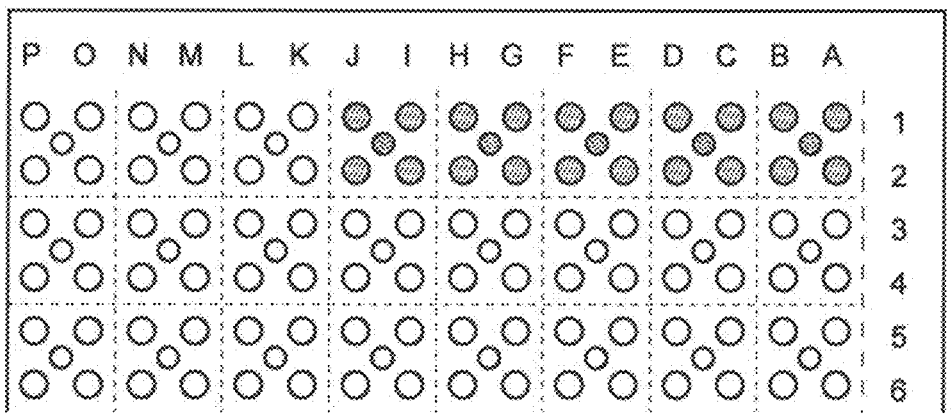
FIG. 4 is another display example of the sample-plate overview area which is displayed when an analysis protocol for laser-power selection is implemented in the present embodiment.
Figure 5:
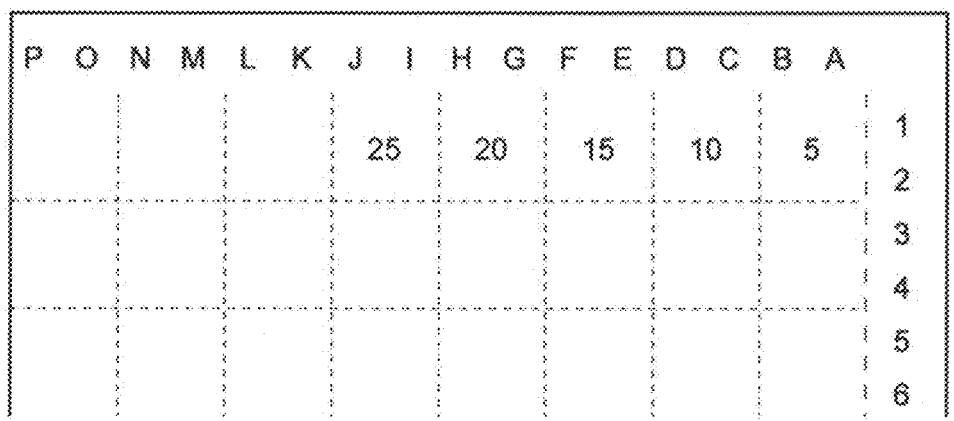
FIG. 5 is still another display example of the sample-plate overview area which is displayed when an analysis protocol for laser-power selection is implemented in the present embodiment.

Putting the label in the previously described manner causes the displayed value of the analysis parameter (in the present case, a candidate value of the laser power) to be superposed on the image of the central well within each individual area 652, as shown in FIG. 3, making it difficult to locate the well in which the calibrant should be placed. To avoid this situation, the present embodiment allows the user to change the display form by appropriately selecting the items in the display-item selector 653. FIG. 4 is a display example of a situation in which the "Well" and "Calibrant well" are selected in the display-item selector 653. FIG. 5 is a display example of a situation in which only the "Label" is selected in the display-item selector 653. When the selection of the items in the display-item selector 653 is changed by the user, the display switcher 44 changes the form of the display in this manner.

Referring to the information displayed on the sample-plate overview area 651 by the sample-position displayer 43, the user arranges the standard sample and the calibrant in the wells of the sample plate 23. The user subsequently presses the file creation button 66, whereupon the batch-file creator 47 creates a batch file for implementing the analysis protocol for laser-power selection and stores the file in the storage section 41.

After the creation of the batch file, the user sets the sample plate 23 on the sample stage 22 and issues a command to initiate the analysis. The measurement executer 48 reads the batch file from the storage section 41 and initiates the measurement. After the beginning of the measurement, the calibrant placed in the first individual area 652 is irradiated with laser light with the intensity set at the first candidate value (5). The detection result of the generated ion is compared with the actual mass-to-charge ratio of the same ion to mass-calibrate the mass analyzer. For example, the mass calibration is achieved by modifying a table which converts the time of flight to the mass-to-charge ratio, which is provided in the mass analyzer or previously stored in the storage section 41. After the measurement of the calibrant, the standard samples placed in the four wells (A1, A2, B1 and B2) within the same individual area 652 are each irradiated with the laser light having the same intensity (5) to generate ions and detect them with the detector 29 after mass-separating them. The output signals from the detector 29 are sequentially stored in the storage section 41. A similar mass spectrometric analysis is also performed on each of the four other individual areas, with the intensity of the irradiating laser light set at the candidate value corresponding to each individual area.

After the measurements for all individual areas 652 concerned have been completed, the analytical processor 49 calculates an average of the detection intensities of each ion obtained by the four mass spectrometric analyses for each individual area 652 and calculates the detection intensities of the ions having mass-to-charge ratios characteristic of the two kinds of peptides which are the measurement targets. Furthermore, the analytical processor 49 determines the ion-detection sensitivity for the laser light having the intensity concerned and determines the candidate value of the laser power with which the total of the detection sensitivities of the ions originating from the two peptides is maximized under the condition that each of the ions originating from the two kinds of peptides can be detected with a sensitivity equal to or higher than a predetermined reference level. The candidate value is stored in the storage section 41. For the present case, it is assumed that the candidate value is 20.

Additionally, the analytical processor 49 displays information concerning the implementation of the protocol for laser-power selection in the analysis-protocol-implementation-information display area 612 of the analysis-protocol selection section 61, in the present embodiment, the displayed information says: "Analysis carried out on //2020". Laser power will be set at 20 in measurements for intensity-ratio calibration, standard plasma analysis and specimen analysis". The laser-power value of 20 is a value determined based on the result obtained by implementing the analysis protocol for laser-power selection.

The protocol-implementation-information collector 45 records the fact that the analysis protocol for laser-power selection has been implemented (for example, information concerning the analysis protocol for laser-power selection, saved in the storage section 41, is updated with a flag which indicates that the protocol has already been implemented).

After the completion of the analysis protocol for laser-power selection, the user removes the sample plate 23 from the analyzing unit 2. Subsequently, the user selects the selector 611 of the next analysis protocol to be implemented (intensity-ratio calibration), whereupon an input of the protocol for intensity-ratio calibration is received by the protocol-selection-input receiver 42. In response to the selection of the analysis protocol, the determiner 46 reads the information of the implementation order of the analysis protocols stored in the storage section 41. The intensity-ratio calibration is an analysis protocol which must be implemented after the analysis protocol for laser-power selection. Accordingly, the determiner 46 checks whether or not the analysis protocol which must be implemented earlier (laser-power selection) has already been implemented. As noted earlier, the fact that the analysis protocol for laser-power selection has already been implemented is recorded by the protocol-implementation-information collector 45. When the fact that the analysis protocol which must be implemented earlier (laser-power selection) has already been implemented is confirmed, the determiner 46 discontinues its operation. If the analysis protocol which must be implemented earlier (laser-power selection) has not yet been implemented, the determiner 46 displays, on the display unit 6, a message to inform that the laser-power selection has not yet been implemented, thereby urging the user to check the situation.

Subsequently, the sample-position displayer 43 reads, from the storage section 41, the sample information and analysis parameters corresponding to the analysis protocol (intensity-ratio calibration) received by the protocol-selection-input receiver 42. As noted earlier, the information stored for the protocol for intensity-ratio calibration includes the use of five kinds of standard samples (IC-1, IC-2, IC-3, IC-4 and IC-5) containing different amounts of peptides which are the measurement targets, as well as analysis parameters including a laser-power value (20) based on the result of the analytical processing in the analysis protocol for laser-power selection. After reading those pieces of information, the sample-position displayer 43 displays those pieces of information at the positions of the wells in which samples are to be placed in the sample-plate overview area 651.

Figure 6:
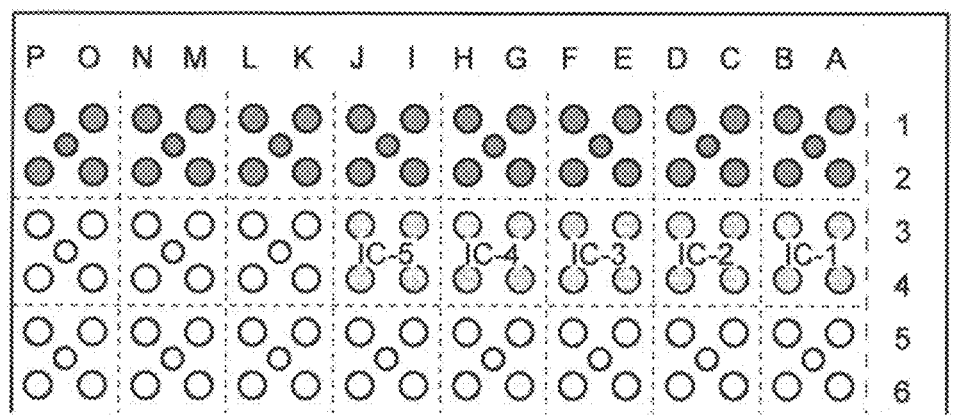
FIG. 6 is a display example of the sample-plate overview area which is displayed when an analysis protocol for intensity-ratio calibration is implemented in the present embodiment.

A display example of the sample-plate overview area 651 by the sample-position displayer 43 is shown in FIG. 6. At this point, five individual areas 652 on the sample plate 23 have already been used for the analysis protocol for laser-power selection. As in the present situation, when there is one or more individual areas 652 which have already been used, the sample-position displayer 43 handles all individual areas 652 in the same horizontal row as already used and shows all wells in those individual areas 652 in gray which indicates that those wells are unusable.

The sample-position displayer 43 subsequently extracts five horizontally arranged individual areas starting from the individual area 652 located at the upper-right corner of the group of unused individual areas 652. Then, the sample-position displayer 43 shows, in the starting-well-number display section 63, the position number of the upper-right well in that individual area 652 (in the present case, "A3").

Figure 7:
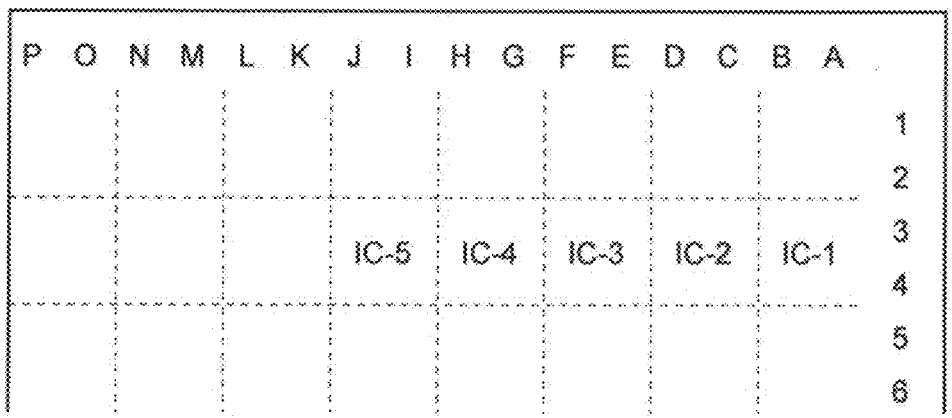
FIG. 7 is another display example of the sample-plate overview area which is displayed when an analysis protocol for intensity-ratio calibration is implemented in the present embodiment.

Next, the sample-position displayer 43 gives specific colors to the five wells in each of the five individual areas 652 in such a manner that the wells at the four corners are shown in green which indicates that the standard sample for intensity-ratio calibration should be placed in those wells, while the central well is shown in purple which indicates that the calibrant should be placed in this well. Similar to FIGS. 3 and 4, the different colors are represented by different hatching patterns in FIG. 6. Additionally, a label is put on each individual area 652 to show the name of the standard sample (IC-1, IC-2, IC-3, IC-4 or IC-5) to be placed in the wells of the individual area 652. The display example in FIG. 6 shows a situation in which all items in the display-item selector 653 are checked. Similar to FIGS. 3-5, the user can change the display form by appropriately selecting the items in the display-item selector 653. FIG. 7 shows a display example of a situation in which only the "Label" is selected among the items in the display-item selector 653.

Referring to the information displayed on the sample-plate overview area 651 by the sample-position displayer 43, the user arranges the five standard samples for intensity-ratio calibration and the calibrant in the wells of the sample plate 23. The user subsequently presses the file creation button 66, whereupon the batch-file creator 47 creates a batch file for implementing the analysis protocol for intensity-ratio calibration and stores the file in the storage section 41.

After the creation of the batch file, the user sets, on the sample stage 22, the sample plate 23 with the five standard samples and the calibrant arranged in the specified wells. When the user subsequently issues a command to initiate the analysis, the measurement executer 48 reads the batch file from the storage section 41 and initiates the measurement. The procedure of the measurement is basically identical to the previously described case of the laser-power selection, and therefore, will not be described. It should be noted that the intensity-ratio calibration uses the same intensity of the laser light (with a laser power of 20) for all samples and calibrant.

After the measurements for all individual areas 652 concerned have been completed, the analytical processor 49 calculates an average of the detection intensities of each ion obtained by the four mass spectrometric analyses for each individual area 652 and determines, from the detection intensities of the ions having the previously specified mass-to-charge ratios (typically, the mass-to-charge ratios of ions characteristic of the two kinds of peptides), the relationship between the content of the target substance in the standard sample and the detection intensities of the ions. Then, the analytical processor 49 determines a correction value for the detection intensity so that the detection intensities of the ions originating from each specified amount of target substance will be previously determined intensities. The correction value is stored in the storage section 41.

Additionally, the analytical processor 49 displays information concerning the implementation of the protocol for intensity-ratio calibration in the analysis-protocol-implementation-information display area 612 of the analysis-protocol selection section 61. In the present embodiment, the displayed information says: "Analysis carried out on //2020".

The protocol-implementation-information collector 45 records the fact that the analysis protocol for intensity-ratio calibration has been implemented (for example, information concerning the analysis protocol for intensity-ratio calibration, saved in the storage section 41, is updated with a flag which indicates that the protocol has already been implemented).

After the completion of the analysis protocol for intensity-ratio calibration, the user removes the sample plate 23 from the analyzing unit 2. The user subsequently selects the next analysis protocol to be implemented. At this point, either the standard plasma analysis or specimen analysis can be implemented. For the present example, it is assumed that the specimen analysis is performed, while the standard plasma analysis is omitted. Then, an input of the protocol for specimen analysis is received by the protocol-selection-input receiver 42. In response to the selection of the analysis protocol, the determiner 46 reads the information of the implementation order of the analysis protocols stored in the storage section 41. The specimen analysis is an analysis protocol which must be implemented after the analysis protocols for both the laser-power selection and intensity-ratio calibration have been completed. Accordingly, the determiner 46 checks whether or not the analysis protocols which must be implemented earlier (laser-power selection and intensity-ratio calibration) have already been implemented. As noted earlier, the fact that the analysis protocols for laser-power selection and intensity-ratio calibration have already been implemented is recorded by the protocol-implementation-information collector 45. When the fact that the analysis protocols which must be implemented earlier laser-power selection and intensity-ratio calibration) have already been implemented is confirmed, the determiner 46 discontinues its operation. If one or both of the analysis protocols which must be implemented earlier (laser-power selection and/or intensity-ratio calibration) have not yet been implemented, the determiner 46 displays, on the display unit 6, the analysis protocol or protocols which have not been implemented yet, thereby urging the user to implement those protocols.

Subsequently, the sample-position displayer 43 reads, from the storage section 41, the sample information and analysis parameters corresponding to the analysis protocol (specimen analysis) received by the protocol-selection-input receiver 42. As noted earlier, the information stored for the protocol for specimen analysis includes the use of the standard plasma and plasma specimens extracted from blood samples taken from untested subjects (in the present example, untested measurement-target samples 1-12 from 12 subjects) as well as analysis parameters including a laser-power value (20) based on the result of the analytical processing in the analysis protocol for laser-power selection. After reading those pieces of information, the sample-position displayer 43 displays those pieces of information at the positions of the wells in which samples are to be placed in the sample-plate overview area 651. It should be noted that a measurement-target sample may be given a long name including the sampling date, the name, gender and age of the subject, as well as many other contents. It is difficult to display such a long sample name within the limited space of the individual area 652. To address this problem, the sample-position displayer 43 in the present embodiment is configured to show the correspondence relationship between the sample names and display codes (S1, S2, . . . ) on the sample-name display area 641, and to display those display codes as labels on the sample-plate overview area 651.

Figure 8:
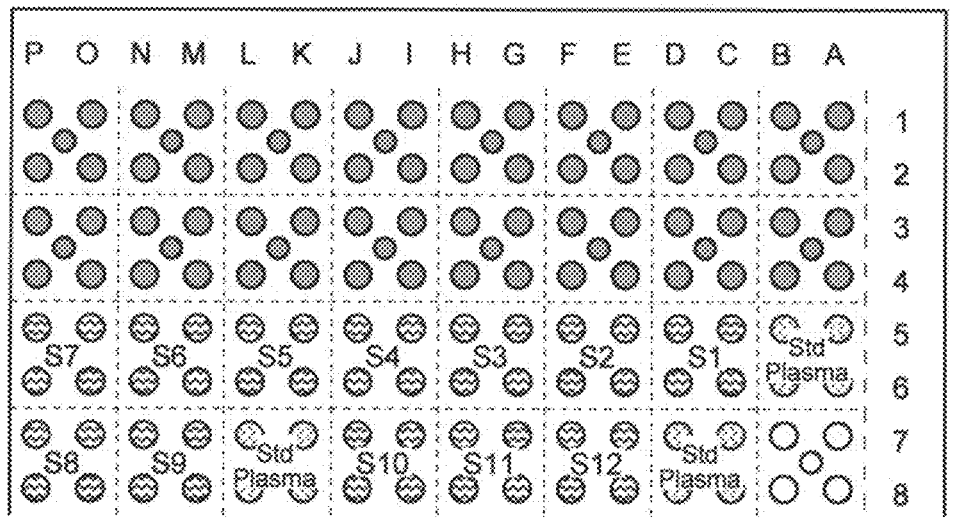
FIG. 8 is a display example of the sample-plate overview area which is displayed when an analysis protocol for specimen analysis is implemented in the present embodiment.

A display example of the sample-plate overview area 651 by the sample-position displayer 43 is shown in FIG. 8. Similar to the previous example, the sample-position displayer 43 handles all individual areas 652 in a row as already used if the row includes one or more individual areas 652 which have already been used. All wells in those individual areas 652 are shown in gray which indicates that those wells are unusable.

The sample-position displayer 43 subsequently locates the individual area 652 at the upper-right corner of the group of unused individual areas 652 and extracts 15 individual areas 652 in a predetermined order starting from the upper-right individual area 652. The reason for extracting 15 individual areas 652 for 12 measurement-target samples is as follows: In the present embodiment, the standard plasma is the first to be subjected to the measurement. Subsequently, a predetermined number of measurement-target samples (in the present example, nine samples) is successively subjected to the measurement, followed by the standard plasma being once more subjected to the measurement. Such a series of measurements are repeated until the completion of the measurement of the last measurement-target sample, followed by the measurement of the last standard plasma. Accordingly, the sample-position displayer 43 extracts 15 individual areas 652 (for one standard plasma, nine measurement-target samples, one standard plasma, three measurement-target samples, and one standard plasma). After the measurement of the sample in the individual area 652 at the end of one row has been completed, the sample in the individual area 652 immediately below that individual area 652 is subjected to the measurement. In other words, when the measurement makes a transition from one row to the next, the measurement turns its moving direction in the rows of the individual areas 652 (from right to left in the first row, and then left to right in the second row). Accordingly, the sample-position displayer 43 should extract 15 individual areas 652 according to this order of measurements. Furthermore, the sample-position displayer 43 shows, in the starting-well-number display section 63, the position number of the upper-right well in the starting individual area 652. This well, which is "A5" in the present case, is the well at which the sample measurement swill be performed first among the four wells in Which samples are to be placed within the individual area 652 concerned.

Figure 9:
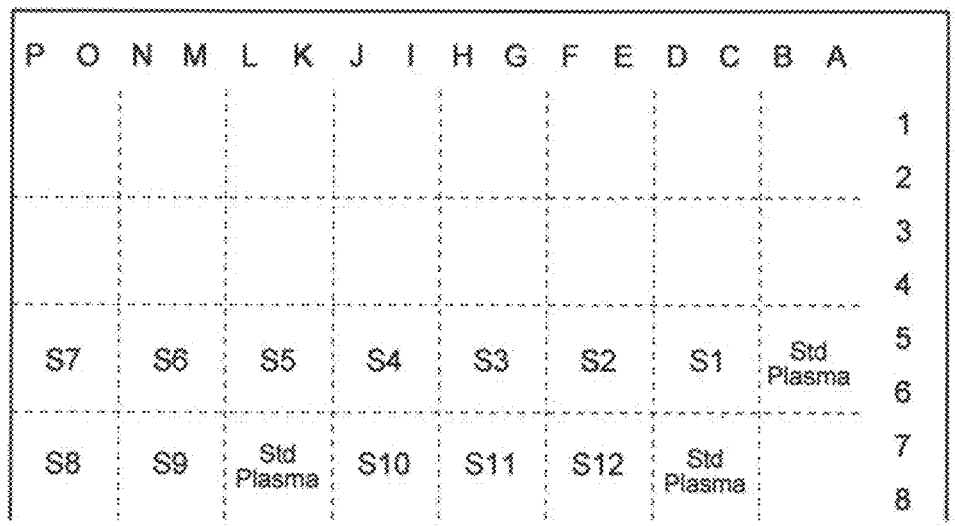
FIG. 9 is another display example of the sample-plate overview area which is displayed when an analysis protocol for specimen analysis is implemented in the present embodiment.

Next, the sample-position displayer 43 gives specific colors to the five wells in each of the $1^{st}$, $11^{th}$ and $15^{th}$ individual areas 652 in such a manner that the wells at the four corners are shown in blue which indicates that the standard plasma should be placed in those wells, while the central well is shown in purple which indicates that the calibrant should be placed in this well. The sample-position displayer 43 also gives specific colors to the five wells in each of the $2^{nd}$ through $10^{th}$ and $12^{th}$ through $14^{th}$ individual areas 652 in such a manner that the wells at the four corners are shown in red which indicates that the measurement-target samples (plasma specimens sampled from untested subjects) should be placed in those wells, while the central well is shown in purple which indicates that the calibrant should be placed in this well. Similar to FIGS. 3, 4 and 6, the different colors are represented by different hatching patterns in FIG. 8. Additionally, each individual area 652 in which the standard plasma should be placed is labeled "StdPlasma", which represents the standard plasma, while each individual area 652 in which a measurement-target sample (1-12) should be placed is labelled with the display code (S1, S2, S3, . . . S12) corresponding to the sample name of the measurement-target sample to be placed in that individual area 652. The display example in FIG. 8 shows a situation in which all items in the display-item selector 653 are checked. As described earlier, the user can change the display form by appropriately selecting the items in the display-item selector 653. FIG. 9 shows a display example of a situation in which only the "Label" is selected among the items in the display-item selector 653.

Referring to the information displayed on the sample-plate overview area 651 by the sample-position displayer 43, the user arranges the standard plasma, measurement-target samples 1-12 and calibrant in the wells of the sample plate 23. The user subsequently presses the file creation button 66, whereupon the batch-file creator 47 creates a batch file for implementing the analysis protocol for specimen analysis and stores the file in the storage section 41.

After the creation of the batch file, the user sets, on the sample stage 22, the sample plate 23 with the standard plasma, measurement-target samples 1-12 and calibrant arranged in the specified wells. When the user subsequently issues a command to initiate the analysis, the measurement executer 48 reads the batch file from the storage section 41 and initiates the measurement. The procedure of the measurement of the calibrant and the standard plasma/measurement-target sample placed in the wells of each individual area 652 is basically identical to the previously described case of the laser-power selection, and therefore, will not be described. It should be noted that, as with the intensity-ratio calibration, the specimen analysis uses the same intensity of the laser light (with a laser power of 20) for all samples and calibrant.

In the specimen analysis, initially, the detection intensities of the ions originating from the two kinds of peptides obtained for the standard plasma are corrected with the correction value calculated in the analysis protocol for intensity-ratio calibration. Subsequently, it is determined whether or not the ratio of the corrected detection intensities of the ions originating from the two kinds of peptides is within a predetermined allowable range from a previously determined value. If the ratio is within the allowable range, the measurements of the measurement-target samples in the next and subsequent individual areas 652 are performed. After the measurements of the measurement-target samples 1-9 have been completed, the measurement of the standard plasma is once more performed in the previously described manner. If the ratio of the corrected detection intensities of the ions originating from the two kinds of peptides is not within the allowable range, a message is displayed on the display unit 6 after the completion of the measurement, informing the user of the fact that there is an abnormality in the measurement result of the standard plasma in question (the ratio of the detection intensities of the ions is not within the allowable range from the previously determined value).

After the measurements for all individual areas 652 concerned have been completed, the analytical processor 49 calculates, for each of the individual areas 652 in which the measurement-target samples were placed, an average of the detection intensities of each ion obtained by the four mass spectrometric analyses, and extracts the detection intensities of the ions having the previously specified mass-to-charge ratios (the mass-to-charge ratios of ions characteristic of the two kinds of peptides). Then, the analytical processor 49 corrects the intensity values with the correction value calculated in the analysis protocol for intensity-ratio calibration. The intensity values of the ions obtained for each measurement-target sample before and after the correction are individually stored in the storage section 41. The analytical processing to be subsequently performed based on those intensity values is identical to the one described in Patent Literature 1, and therefore, will not be described.

Thus, in the analyzing system 1 according to the present embodiment, when each analysis protocol is going to be implemented, the sample-position displayer 43 displays, in the sample-plate overview area 651, the positions of the wells in which samples are to be arranged, and information concerning the samples to be arranged. Therefore, when implementing each protocol, the user can conveniently understand which sample should be placed at which position, and correctly arrange the samples.

In the analyzing system 1 according to the present embodiment, the protocol-implementation-information collector 45 records the fact that each analysis protocol has been implemented. When an analysis protocol has been selected by the user, the batch file creator 47 creates a batch file for implementing the selected analysis protocol, after it is confirmed by the determiner 46 that an analysis protocol or protocols which must be implemented earlier than the selected analysis protocol have already been completed. In other words, if the user selects a protocol without implementing another protocol which must be implemented earlier, the batch file for implementing the selected protocol will not be created. Therefore, the user can be appropriately instructed to implement the plurality of protocols in the correct order.

In the analyzing system 1 according to the present embodiment, when there is a row including one or more individual areas 652 which have already been used, the sample-position displayer 43 handles all individual areas 652 in that row as already used and designates the individual area 652 at the right end of the next row as the starting well. This lowers the probability that the user incorrectly recognizes the position of the individual area 652 in which the first sample should be placed.

In the analyzing system 1 according to the present embodiment, each well in the individual areas 652 is given a display color corresponding to the kind of sample to be placed in that well. This lowers the probability that the user places an incorrect sample in the well. Additionally, as in the case of the analysis protocol for laser-power selection, when the same sample is placed in the individual areas 652 and subjected to a measurement using a different value of an analysis parameter for each individual area 652, the value of the parameter is shown in the form of a label. As in the case of the analysis protocol for intensity-ratio calibration or specimen analysis, when different samples are respectively placed in the individual areas 652, a label related to each sample is displayed on each individual area 652. This allows the user to conveniently recognize what kind of sample should be placed in which individual area 652 as well as what value of the analysis parameter should be used in the measurement.

The previous embodiment is a mere example and can be appropriately modified within the spirit and scope of the present invention. Although the previous embodiment is concerned with an analyzing system 1 including a MALDI-TOF mass analyzer, an appropriate type of analyzing device may be used according to the purpose or content of the analysis.

In the previous embodiment, the analytical operation assisting device and program are included in a section of the controlling-and-processing unit 4. The device and program may be separated from the controlling-and-processing unit 4.

Figure 10:
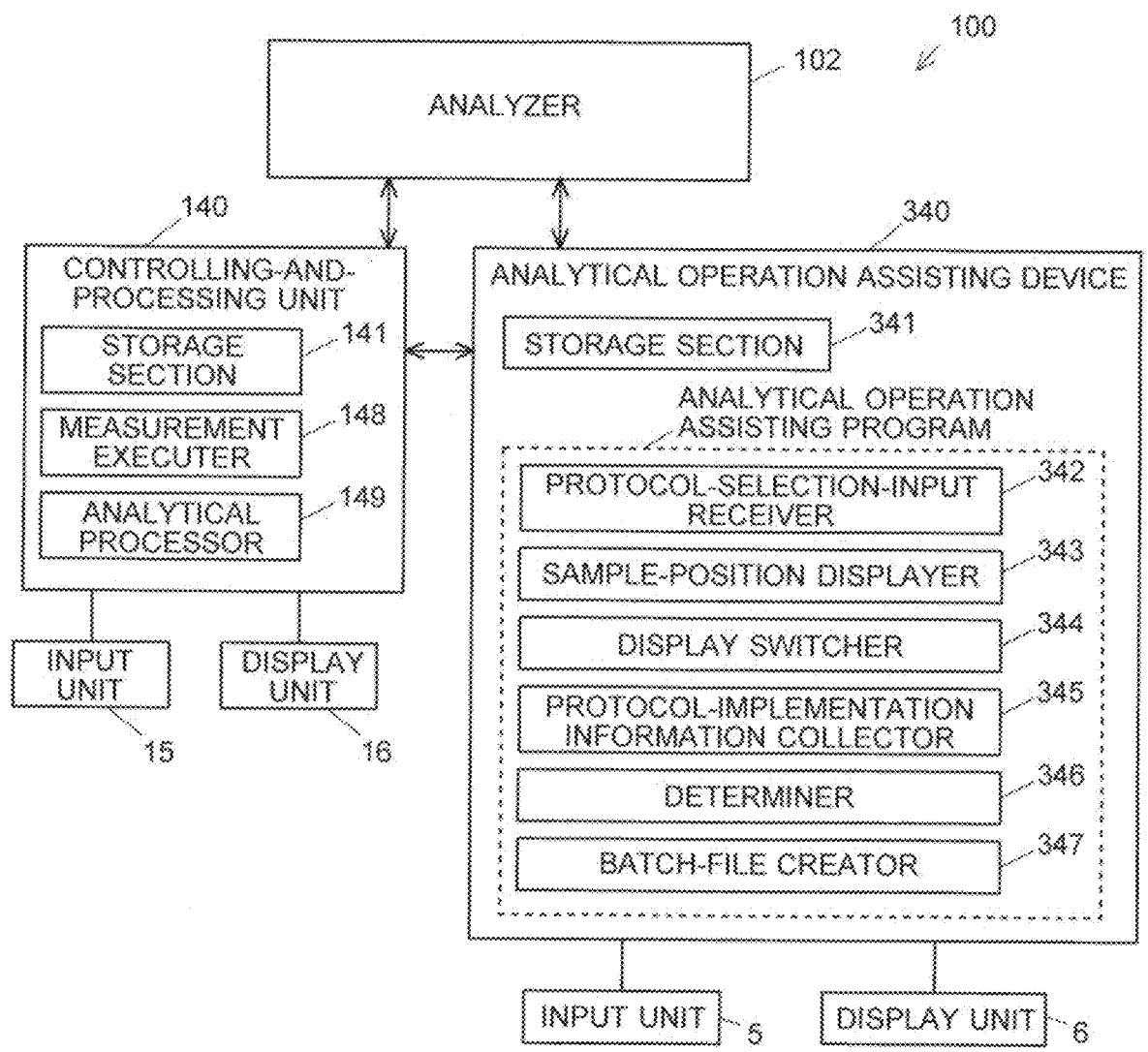
FIG. 10 is a configuration diagram showing the main components of an analyzing system according to a modified example.

FIG. 10 shows the configuration of the main components of an analyzing system 100 as a modified example. The analyzing system 100 according to the modified example includes an analyzer 102, controlling-and-processing unit 140 and analytical operation assisting device 340. These components can communicate with each other. The analyzer 102 may be a mass analyzer as in the previous embodiment or a different type of analyzer.

The controlling-and-processing unit 140 is mainly in charge of the control of the operation of the components in the analyzer 102 and the analytical processing. The controlling-and-processing unit 140 includes, in addition to the storage section 141, a measurement executer 148 and an analytical processor 149 as its functional blocks. The specific functions of the measurement executer 148 and the analytical processor 149 are identical to those of the previous embodiment, and therefore, will not be described. The controlling-and-processing unit 140 is actually a common personal computer, on which the aforementioned functional blocks are embodied by running a pre-installed analysis program on a processor of the computer. Additionally, an input unit 15 and a display unit 16 are connected to the controlling-and-processing unit 140.

The analytical operation assisting device 340 is a device for assisting a user in the analytical operations, and particularly, in the task of arranging samples in the sample plate 23. The analytical operation assisting device 340 includes, in addition to the storage section 341, a protocol-selection-input receiver 342, sample-position displayer 343, display switcher 344, protocol-implementation-information collector 345, determiner 346 and batch-file creator 347 as its functional blocks. The specific functions of these functional blocks are identical to those of the previous embodiment, and therefore, will not be described. The analytical operation assisting device 340 is also actually a common personal computer, on which the aforementioned functional blocks are embodied by running a pre-installed analysis program on a processor of the computer. The analytical operation assisting device 340 also has an input unit 35 and a display unit 36 connected.

The various items of information stored in the storage section 41 in the analyzing system 1 according to the previous embodiment are stored in either the storage section 141 of the controlling-and-processing unit 140 or the storage section 341 of the analytical operation assisting device 340, or in both of them. When the same set of information is stored in both storage sections, the information can be synchronized between the storage sections 141 and 341 for every update of the information.

MODES OF INVENTION

A person skilled in the art can understand that the previously described illustrative embodiments are specific examples of the following modes of the present invention.

Clause 1

One mode of the present invention is an analytical operation assisting device configured to be capable of communicating with an analyzing device in which a sample-containing member is to be set, and to assist a user in analytical operations which include arranging samples in a plurality of sample-placement portions provided in the sample-containing member and sequentially implementing a plurality of protocols, the analytical operation assisting device including:

a storage section in which analysis conditions and information concerning the order of implementation of the plurality of protocols are stored, the analysis conditions including information concerning samples to be arranged in each of the plurality of protocols and an analysis parameter;

a display unit;

a protocol-selection-input receiver configured to receive an input of the selection of one of the plurality of protocols;

a sample-position displayer configured to read, from the storage section, the information concerning the samples to be arranged in the protocol inputted through the protocol-selection-input receiver, and to display, on the display unit, the read information along with the positions of the plurality of sample-placement portions provided in the sample-containing member;

a protocol-implementation-information collector configured to collect, from the analyzing device, information concerning the state of implementation of the plurality of protocols;

a determiner configured to determine whether or not a protocol which must be implemented earlier than the protocol inputted through the protocol-selection-input receiver was already implemented, based on the stale of implementation of the plurality of protocols collected by the protocol-implementation-information collector and the order of implementation of the plurality of protocols stored in the storage section; and a batch-file creator configured to read, from the storage section, the analysis conditions corresponding to the protocol inputted through the protocol-selection-input receiver and to create a batch file for implementing the selected protocol, when it is determined by the determiner that the protocol which must be implemented earlier was already implemented.

Clause 6

Another mode of the present invention is a non-transitory computer readable medium recording a program for enabling a computer to communicate with an analyzing device in which a sample-containing member is to be set, and for assisting a user in analytical operations which include arranging samples in a plurality of sample-placement portions provided in the sample-containing member and sequentially implementing a plurality of protocols, where the computer includes:

a storage section in which analysis conditions and information concerning the order of implementation of the plurality of protocols are stored, the analysis conditions including information concerning samples to be arranged in each of the plurality of protocols and an analysis parameter; and a display unit;

and the program is configured to make the computer function as:

a protocol-selection-input receiver configured to receive an input of the selection of one of the plurality of protocols;

a sample-position displayer configured to read, from the storage section, the information concerning the samples to be arranged in the protocol inputted through the protocol-selection-input receiver, and to display, on the display unit, the read information along with the positions of the plurality of sample-placement portions provided in the sample-containing member;

a protocol-implementation-information collector configured to collect, from the analyzing device, information concerning the state of implementation of the plurality of protocols;

a determiner configured to determine whether or not a protocol which must be implemented earlier than the protocol inputted through the protocol-selection-input receiver was already implemented, based on the state of implementation of the plurality of protocols collected by the protocol-implementation-information collector and the order of implementation of the plurality of protocols stored in the storage section; and a batch-file creator configured to read, from the storage section, the analysis conditions corresponding to the protocol inputted through the protocol-selection-input receiver and to create a batch file for implementing the selected protocol, when it is determined by the determiner that the protocol which must be implemented earlier was already implemented.

In the analytical operation assisting device described in Clause 1 and the non-transitory computer readable medium recoding an analytical operation assisting program described in Clause 6, when a user selects one of the plurality of protocols previously stored in the storage section, the sample-position displayer reads, from the storage section, the information concerning the samples to be arranged in the selected protocol, and displays the read information along with the positions of the plurality of sample-placement portions provided in the sample-containing member. For example, in the case of where the sample plate has a plurality of sample-placement portions arranged in a lattice form, the sample information is displayed on the same number of sample-placement portions as the samples to be arranged in the protocol concerned, starting from the sample-placement portion located at the upper-right corner of the sample plate displayed in a predetermined orientation on the screen. Therefore, when implementing each protocol, the user can conveniently understand which sample should be placed at which position, and correctly arrange the samples.

Furthermore, in the analytical operation assisting device described in Clause 1 and the non-transitory computer readable medium recoding a program for assisting in analytical operations described in Clause 6, when a protocol is selected by the user, whether or not a protocol which must be implemented earlier than the selected protocol was already implemented is determined by the determiner. When it is confirmed that the protocol which must be implemented earlier was already implemented, a batch file for implementing the protocol selected by the user is created. In other words, if the user selects a protocol without implementing another protocol which must be implemented earlier, the batch file for implementing the selected protocol will not be created. Therefore, the user can be appropriately instructed to implement the plurality of protocols in the correct order.

Clause 2

The analytical operation assisting device described in Clause 1 may further be configured as follows:

the plurality of sample-placement portions are provided in a lattice form; and the sample-position displayer is configured to handle all sample-placement portions forming a line in a direction defined by the lattice form as already used if any one of the sample-placement portions forming the line is already used, and to display the plurality of sample-placement portions so that the already used sample-placement portions are distinguishable from unused sample-placement portions.

In the analytical operation assisting device described in Clause 2, all sample-placement portions forming a row or column in the predetermined direction are handled as already used. This lowers the probability that the user incorrectly recognizes the starting point from which samples should be arranged.

Clause 3

In the analytical operation assisting device described in Clause 2, the sample-position displayer may be configured to display information concerning the samples to be arranged, starting from the sample-placement portion located at a previously specified corner among the unused sample-placement portions.

In the analytical operation assisting device described in Clause 3, the task of arranging samples always starts from a sample-placement portion located at a previously specified corner, regardless of the protocol. This further lowers the probability that the user incorrectly recognizes the starting point from which samples should be arranged.

Clause 4

In the analytical operation assisting device described in one of Clauses 1-3, the sample-position displayer may be configured to display each of the sample-placement portions in a visually distinguishable manner that depends on the kind of sample to be placed.

When a plurality of protocols are implemented, not only actual measurement-target samples but also a standard sample depending on the purpose of each protocol may be subjected to the measurement. The analytical operation assisting device described in Clause 4 displays each sample-placement portion in a visually distinguishable manner that depends on the kind of sample. This lowers the probability that an incorrect kind of sample is placed.

Clause 5

In the analytical operation assisting device described in one of Clauses 1-4, the sample-position displayer may be configured to display text information for identifying each sample when the samples to be placed include a plurality of samples which are of the same kind yet are different from each other in a specific aspect.

In a measurement of target samples respectively collected from a plurality of subjects, or in a measurement of standard samples each of which contains a different specified amount of target substance, all samples are of the same kind. As in these cases, when a plurality of samples of the same kind yet different from each other in a specific aspect are to be arranged, the analytical operation assisting device described in Clause 5 displays text information by which those samples can be distinguished from each other. This helps the user correctly arrange those samples.

REFERENCE SIGNS LIST 1, 100 . . . Analyzing System
102 . . . Analyzer
2 . . . Analyzing Unit
22 . . . Sample Stage
23 . . . Sample Plate
26 . . . Laser Irradiator
27 . . . Mirror
28 . . . Flight Tube
29 . . . Detector
4, 140 . . . Controlling-and-Processing Unit
41, 141, 341 . . . Storage Section
42, 342 . . . Protocol-Selection-Input Receiver
43, 343 . . . Sample-Position Displayer
44, 344 . . . Display Switcher
45, 345 . . . Protocol-Implementation-information Collector
46, 346 . . . Determiner
47, 347 . . . Batch-File Creator
48, 148 . . . Measurement Executer
49, 149 . . . Analytical Processor
5, 15, 35 . . . Input Unit
6, 16, 36 . . . Display Unit
61 . . . Analysis-Protocol Selection Section
611 . . . Selector
612 . . . Analysis-Protocol-Implementation-Information Display Area
62 . . . Dataset-Name Input Section
63 . . . Starting-Well-Number Display Section
64 . . . Sample-Information Display Section
641 . . . Sample-Name Display Area
642 . . . Data-Editing Button
65 . . . Sample-Plate Display Section
651 . . . Sample-Plate Overview Area
652 . . . Individual Area
653 . . . Display-Item Selector
66 . . . File Creation Button

The invention claimed is:

1. An analytical operation assisting device configured to be capable of communicating with an analyzing device in which a sample-containing member is to be set, and to assist a user in analytical operations which include arranging samples in a plurality of sample-placement portions provided in the sample-containing member and sequentially implementing a plurality of protocols, the analytical operation assisting device comprising:
   a storage section in which analysis conditions and information concerning an order of implementation of the plurality of protocols are stored, the analysis conditions including information concerning samples to be arranged in each of the plurality of protocols and an analysis parameter;
   a display unit;
   a protocol-selection-input receiver configured to receive an input of a selection of one of the plurality of protocols;
   a sample-position displayer configured to read, from the storage section, the information concerning the samples to be arranged in the protocol inputted through the protocol-selection-input receiver, and to display, on the display unit, the read information along with positions of the plurality of sample-placement portions provided in the sample-containing member;
   a protocol-implementation-information collector configured to collect, from the analyzing device, information concerning a state of implementation of the plurality of protocols;
   a determiner configured to determine whether or not a protocol which must be implemented earlier than the protocol inputted through the protocol-selection-input receiver was already implemented, based on the state of implementation of the plurality of protocols collected by the protocol-implementation-information collector and the order of implementation of the plurality of protocols stored in the storage section; and
   a batch-file creator configured to read, from the storage section, the analysis conditions corresponding to the protocol inputted through the protocol-selection-input receiver and to create a batch file for implementing the selected protocol, when it is determined by the determiner that the protocol which must be implemented earlier was already implemented.

2. The analytical operation assisting device according to claim 1, wherein:
   the plurality of sample-placement portions are provided in a lattice form; and
   the sample-position displayer is configured to handle all sample-placement portions forming a line in a direction defined by the lattice form as already used if any one of the sample-placement portions forming the line is already used, and to display the plurality of sample-placement portions so that the already used sample-placement portions are distinguishable from unused sample-placement portions.

3. The analytical operation assisting device according to claim 2, wherein:
the sample-position displayer is configured to display information concerning the samples to be arranged, starting from the sample-placement portion located at a previously specified corner among the unused sample-placement portions.

4. The analytical operation assisting device according to claim 1, wherein:
the sample-position displayer is configured to display each of the sample-placement portions in a visually distinguishable manner that depends on a kind of sample to be placed.

5. The analytical operation assisting device according to claim 1, wherein:
the sample-position displayer is configured to display text information for identifying each sample when the samples to be placed include a plurality of samples which are of a same kind yet are different from each other in a specific aspect.

6. A non-transitory computer readable medium recording program for enabling a computer to communicate with an analyzing device in which a sample-containing member is to be set, and for assisting a user in analytical operations which include arranging samples in a plurality of sample-placement portions provided in the sample-containing member and sequentially implementing a plurality of protocols, wherein: the computer includes:
a storage section in which analysis conditions and information concerning an order of implementation of the plurality of protocols are stored, the analysis conditions including information concerning samples to be arranged in each of the plurality of protocols and an analysis parameter; and
a display unit;
and the program is configured to make the computer function as:
a protocol-selection-input receiver configured to receive an input of a selection of one of the plurality of protocols;
a sample-position displayer configured to read, from the storage section, the information concerning the samples to be arranged in the protocol inputted through the protocol-selection-input receiver, and to display, on the display unit, the read information along with positions of the plurality of sample-placement portions provided in the sample-containing member;
a protocol-implementation-information collector configured to collect, from the analyzing device, information concerning a state of implementation of the plurality of protocols;
a determiner configured to determine whether or not a protocol which must be implemented earlier than the protocol inputted through the protocol-selection-input receiver was already implemented, based on the state of implementation of the plurality of protocols collected by the protocol-implementation-information collector and the order of implementation of the plurality of protocols stored in the storage section; and
a batch-file creator configured to read, from the storage section, the analysis conditions corresponding to the protocol inputted through the protocol-selection-input receiver and to create a batch file for implementing the selected protocol, when it is determined by the determiner that the protocol which must be implemented earlier was already implemented.

* * * * *